US010113953B2

(12) United States Patent
Babin et al.

(10) Patent No.: US 10,113,953 B2
(45) Date of Patent: Oct. 30, 2018

(54) METHOD AND DEVICE FOR DETERMINING THE PRESENCE OF A SPILL OF A PETROLEUM PRODUCT BY THE DETECTION OF A PETROLEUM-DERIVED VOLATILE ORGANIC COMPOUND

(71) Applicant: INSTITUT NATIONAL D'OPTIQUE, Québec (CA)

(72) Inventors: François Babin, Québec (CA); Jean-François Gravel, Québec (CA); Pascal Dufour, Québec (CA)

(*) Notice: Subject to any disclaimer, the term of this patent is extended or adjusted under 35 U.S.C. 154(b) by 18 days.

(21) Appl. No.: 15/679,359

(22) Filed: Aug. 17, 2017

(65) Prior Publication Data
US 2018/0052100 A1   Feb. 22, 2018

Related U.S. Application Data

(60) Provisional application No. 62/377,961, filed on Aug. 22, 2016.

(51) Int. Cl.
*G01N 21/33* (2006.01)
*G01N 21/65* (2006.01)
(Continued)

(52) U.S. Cl.
CPC ............. *G01N 21/33* (2013.01); *G01J 3/44* (2013.01); *G01M 3/18* (2013.01); *G01M 3/38* (2013.01);
(Continued)

(58) Field of Classification Search
CPC ............................... G01N 21/33; G01N 21/65
(Continued)

(56) References Cited

U.S. PATENT DOCUMENTS 2,974,226 A * 3/1961 Fisher ................... G01N 21/33
250/372
6,040,191 A   3/2000 Grow
(Continued)

FOREIGN PATENT DOCUMENTS

WO        2010112531 A1    10/2010

OTHER PUBLICATIONS

Adam Willitsford et al., "Resonance enhanced Raman scatter in liquid benzene at vapor-phase absorption peaks", Optics Express, vol. 21 No. 22, Oct. 24, 2013, pp. 26150-26161, United States.
(Continued)

*Primary Examiner* — David Porta
*Assistant Examiner* — Gisselle Gutierrez
(74) *Attorney, Agent, or Firm* — Norton Rose Fulbright Canada LLP; Alexandre Daoust

(57) ABSTRACT

The method of determining the presence of a spill of a petroleum product by the detection of a petroleum-derived volatile organic compound (VOC) generally has a step of providing an ultraviolet (UV) radiation generator and a receiver assembly aimed at a scene; a step of illuminating a distant target in the scene with a UV radiation beam, the UV radiation beam having an excitation wavelength being tuned to a resonance Raman excitation wavelength of the petroleum derived VOC; a step of receiving a return signal from the distant target; and a step of determining the presence of the petroleum-derived VOC upon detecting Raman scattering in the received return signal, the Raman scattering being indicative of a resonance Raman interaction between the UV radiation beam and molecules of the petroleum-derived VOC.

17 Claims, 10 Drawing Sheets

(51) Int. Cl.
  *G01M 3/18* (2006.01)
  *G01J 3/44* (2006.01)
  *G01M 3/38* (2006.01)
  *G01N 21/94* (2006.01)
  *G01N 21/17* (2006.01)

(52) U.S. Cl.
  CPC ............ *G01N 21/65* (2013.01); *G01N 21/94* (2013.01); *G01N 2021/1797* (2013.01); *G01N 2201/0214* (2013.01)

(58) Field of Classification Search
  USPC ........................................................ 250/372
  See application file for complete search history.

(56) References Cited

U.S. PATENT DOCUMENTS

| | | | |
|---|---|---|---|
| 6,377,828 B1 | 4/2002 | Chaiken et al. | |
| 7,027,924 B2* | 4/2006 | Spoonhower | G01M 3/005 250/253 |
| 7,139,072 B1* | 11/2006 | Boss | G01J 3/02 356/301 |
| 7,973,926 B1* | 7/2011 | Uibel | G01N 33/2835 356/301 |
| 2009/0219525 A1* | 9/2009 | Marcus | G01J 3/02 356/301 |
| 2010/0241357 A1 | 9/2010 | Chan et al. | |
| 2011/0309248 A1* | 12/2011 | Thoma | G01J 1/0407 250/339.06 |
| 2012/0099102 A1 | 4/2012 | Bello | |
| 2012/0162641 A1 | 6/2012 | Schmidt et al. | |
| 2014/0253919 A1 | 9/2014 | Yui | |
| 2015/0064778 A1 | 3/2015 | Yamada | |
| 2016/0116414 A1 | 4/2016 | Day et al. | |

OTHER PUBLICATIONS

Howard S. Sands et al. "UV-Excited Resonance Raman Spectroscopy of Narcotics and Explosives", Journal of Forensic Sciences, vol. 43, No. 3, 1998, pp. 509-513, United States.

Anneli Ehlerding et al. "Resonance-Enhanced Raman Spectroscopy on Explosives Vapor at Standoff Distances", International Journal of Spectroscopy, vol. 2012, Article ID 158715, Nov. 2, 2011, pp. 1-9, Sweden.

Roberto Chirico et al., "Stand-off detection of traces of explosives and precursors on fabrics by UV raman spectroscopy", Optics and Photonics for Counterterrorism, Crime Fighting, and Defence VIII, vol. 8546, 2012, pp. 1-5, Italy.

M. Gaft et al., "UV gated Raman spectroscopy for standoff detection of explosives", Optical Materials 30, Jan. 2, 2008, pp. 1739-1746, United States.

* cited by examiner

METHOD AND DEVICE FOR DETERMINING THE PRESENCE OF A SPILL OF A PETROLEUM PRODUCT BY THE DETECTION OF A PETROLEUM-DERIVED VOLATILE ORGANIC COMPOUND

FIELD

The improvements generally relate to the field of trace contaminant or pollutant detection and more specifically relate to detectors involving Raman scattering.

BACKGROUND

The oil and gas industry has developed multiple techniques to detect spills of petroleum products. One significant source of spills is pipeline leaks. One technique pertaining to pipelines involves monitoring pressure drops along a pipeline using pressure sensors all along the pipeline. One other technique involves moving an acoustic detection apparatus above the pipeline while listening for a sound indicative of a leak.

As can be understood, preventing a pipeline from leaking, no matter how small the leak may be, is of great interest, both from environmental and economic perspectives. Although the existing spill detection techniques are satisfactory to a certain degree, there remains room for improvement.

SUMMARY

In accordance with one aspect, there is provided a system and method to detect spills of petroleum products. It is to be understood that spills encompass petroleum products in any phase of matter, solid, liquid or vapor. The system and method can include using a device. The device can include a UV radiation generator, such as a UV laser, having a wavelength selected specifically (tuned) to target a resonance Raman excitation wavelength of a molecule which is known to be indicative of a petroleum product spill. The device can also include a detector which is used to detect a return signal from an area which is subjected to the UV radiation beam. The detection of emissions from the area at a wavelength which corresponds to Raman scattering from the resonance Raman excitation radiation can then be associated to the presence of a petroleum product spill. The device can be embodied in various forms to detect spills from correspondingly various sources. For instance, the device can be mounted to an aircraft or to another form of vehicle (e.g. boat) to detect and/or monitor the presence of a spill on a greater area of land or sea. Alternately, the device can be mounted to a fixed structure and either be aimed at a fixed location or moved (e.g. rotated) to scan a given area.

In accordance with one aspect, there is provided a method of determining the presence of a spill of a petroleum product by the detection of a petroleum-derived volatile organic compound (VOC), the method comprising: providing an ultraviolet (UV) radiation generator and a receiver assembly aimed at a scene; the UV radiation generator illuminating a distant target in the scene with a UV radiation beam, the UV radiation beam having an excitation wavelength being tuned to a resonance Raman excitation wavelength of the petroleum derived VOC; the receiver assembly receiving a return signal from the distant target; and determining the spill of the petroleum product upon detecting Raman scattering in the received return signal, the Raman scattering being indicative of a resonance Raman interaction between the UV radiation beam and molecules of the petroleum-derived VOC.

In accordance with another aspect, there is provided a device for determining the presence of a spill of a petroleum product by the detection of a petroleum-derived VOC, the device comprising: a housing; an UV radiation generator mounted to the housing and adapted to illuminate a distant target in a scene with a UV radiation beam, the UV radiation emitter being adapted to generate the UV radiation beam at an emission wavelength tuned to a resonance Raman wavelength of the petroleum-derived VOC; a receiver assembly mounted to the housing and adapted to receive a return signal from the distant target; and a computer configured to operate the UV radiation emitter and the receiver to determine the presence of the spill of the petroleum product upon identifying Raman scattering in the received return signal, the Raman scattering being indicative of a resonance Raman interaction between the UV radiation beam and molecules of the petroleum-derived VOC. Such a device may be used to detect the presence of a spill of petroleum product by the detection of a petroleum-derived VOC.

In accordance with another aspect, there is provided a computer-implemented method of determining the presence of a spill of a petroleum product by the detection of a petroleum-derived VOC, the computer-implemented method comprising: instructing an UV radiation generator to generate a UV radiation beam aimed at a distant target, the UV radiation beam having an excitation wavelength being tuned to a resonance Raman wavelength of the petroleum-derived VOC; operating a receiver assembly to receive a return signal from the distant target; and determining the presence of the spill of the petroleum product based on the received return signal when the received return signal includes Raman scattering being indicative of a Raman resonance interaction between the UV radiation beam and molecules of the petroleum-derived VOC.

Many further features and combinations thereof concerning the present improvements will appear to those skilled in the art following a reading of the instant disclosure.

DESCRIPTION OF THE FIGURES

In the figures.

DETAILED DESCRIPTION

Figure 1:
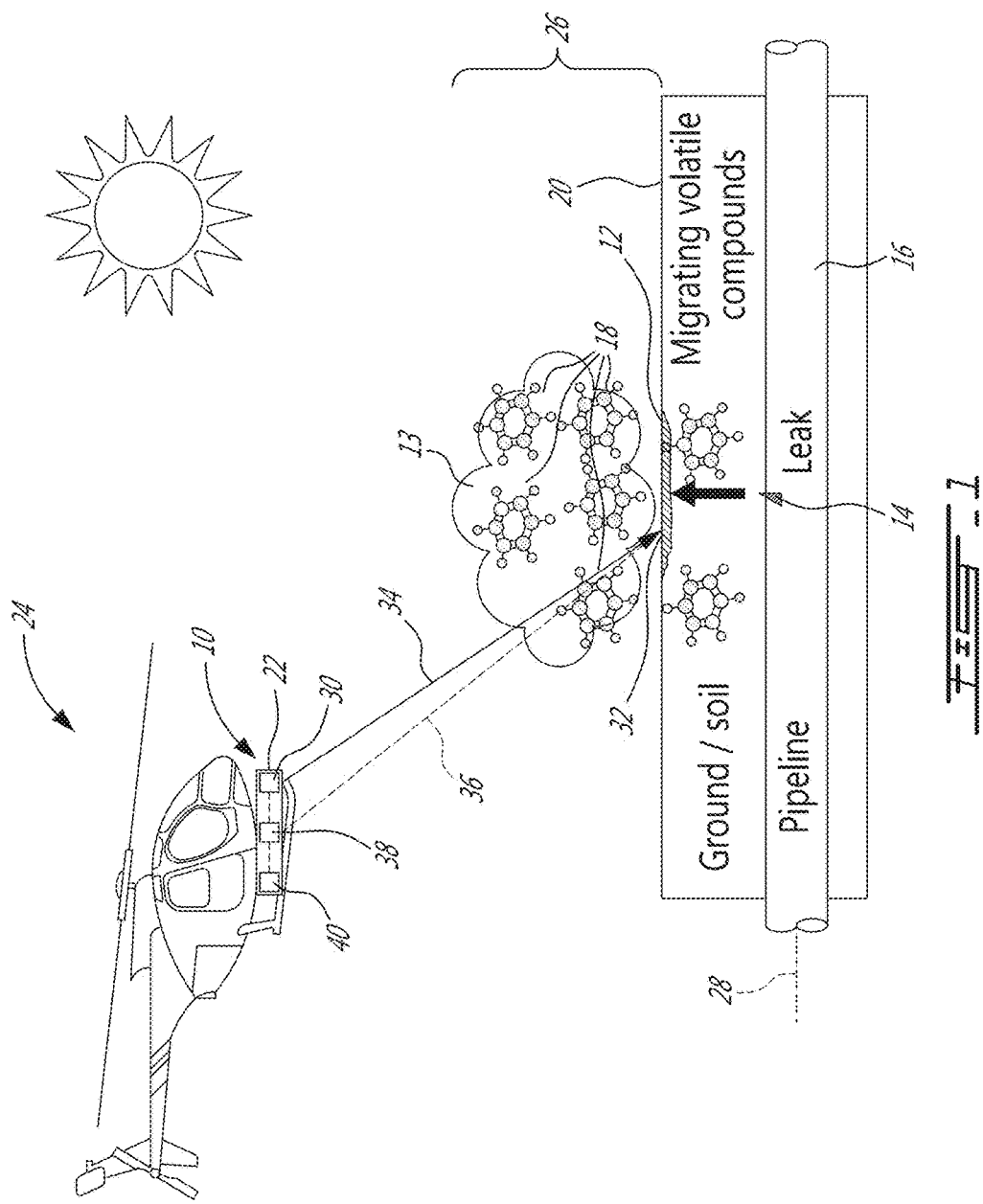
FIG. 1 is a schematic view of an example of a device for determining the presence of a spill of petroleum product using the presence of a VOC contained in the spill, in accordance with an embodiment.

FIG. 1 shows an example of a device 10 for determining the presence of a distant spill 12 of liquid petroleum product via the presence of a vapor plume 13 of petroleum-derived volatile organic compound (VOC). In this disclosure, the term spill is used so as to encompass any kind of spill such as pools, slicks and gas/vapor leaks. The spill can be caused by a leak in a pipeline, buried or above ground, in a storage facility (tank, tank farm, truck, ship and the like), by spilling a product in transfer operations, or from vapors originating from open liquid/solid containers or leaks in vapor phase storage containers. Examples of petroleum-derived VOCs can include benzene, toluene, ethylbenzene, xylene, naphthalene, styrene and any other VOC that may derive from the petroleum product.

In some embodiments, such as the one depicted in FIG. 1, the spill 12 originates from a leak 14 along a buried pipeline 16. In such an example, molecules 18 of the leaked petroleum-derived VOC gradually migrate through the ground and collectively form part of the spill 12 as they break the surface 20. A plume 13 of the petroleum-derived VOC may be present.

It is understood that, however, in some other embodiments, the origin of the spill of petroleum can differ. For instance, the spill can originate from an underground spill or an open-air spill such as an aboveground spill, a sea level spill and the like. The spill can originate from a leaked pipeline or from a failure of an oil delivery vehicle.

As depicted in this example, the device 10 has a housing 22 mountable to an aircraft 24. In some embodiments, the aircraft 24 is a manned aircraft such as an airplane or a helicopter. In some other embodiments, the aircraft 24 is an unmanned aircraft such as a drone. Any other suitable type of aircraft can be used.

The aircraft 24 is used to fly the device 10 over a scene 26. For instance, the aircraft 24 can fly the device 10 at multiple tens of kilometers per hour at an altitude of about 100 meters above the surface 20, and without disrupting normal operation of the buried pipeline 16.

As depicted in the illustrated embodiment, the aircraft 24 is used to fly the device 10 over a pipeline path 28 of the buried pipeline 16. In alternate embodiments, the aircraft 24 is used to fly the device 10 over a land, a sea or any other area that may present spills of petroleum products.

The device 10 has an ultraviolet (UV) radiation generator 30 mounted to the housing 22. The UV radiation generator 30 is adapted to illuminate a distant target 32 in the scene 26 with a UV radiation beam 34 as the aircraft 24 flies over the scene 26. In FIG. 1, the distant target 32 is illustrated to coincide with the spill of petroleum product. However, in some other embodiments, it is understood that the distant target can coincide with a plume of petroleum-derived VOC, i.e. a point above the surface 20. Any point in space can be a distant target as long as the point in space is in the field-of-operation of the device 10.

More specifically, the UV radiation generator 30 is adapted to generate the UV radiation beam 34 at an excitation wavelength $\lambda e$ that is tuned to a resonance Raman excitation wavelength of the petroleum-derived VOC under examination. A receiver assembly 38 is mounted to the housing 22 and adapted to receive a return signal 36 from the distant target 32. A computer 40 is provided to determine the presence of a distant spill 12 of petroleum product via the presence of petroleum-derived VOC upon detecting Raman scattering in the received return signal 36.

In some embodiments, the receiver assembly 38 includes a spectrometer. In these embodiments, the detected Raman scattering corresponds to a Raman spectrum of the petroleum-derived VOC. For instance, the detected Raman spectrum can have at least one Raman peak at a given Raman shift for the UV radiation beam 34 used which is indicative of the presence of the petroleum-derived VOC under examination.

In some other embodiments, the receiver assembly 38 includes an intensity detector. In these embodiments, the detected Raman scattering corresponds to a given intensity (e.g., above a threshold) in an expected Raman scattering band for the UV radiation beam 34 used. As will be understood, the expected Raman scattering band can vary as a function of the resonance Raman excitation wavelength.

In some embodiments, the computer 40 operates the UV radiation generator and the receiver assembly in a synchronized manner allowing to determine a spill 12 of petroleum-derived VOC at a predetermined range. For instance, the UV radiation generator 30 and the receiver assembly 38 may be used in a light detection and ranging (LIDAR) configuration. In this way, the measurement can be said to be spatially-resolved or time-resolved.

The Raman scattering is indicative of a resonance Raman interaction between the UV radiation beam 34 and molecules 18 of the petroleum-derived VOC.

As will be understood, a resonance Raman interaction refers to a type of Raman scattering interaction wherein the excitation wavelength $\lambda e$ is selected so as to be close in energy to an electronic transition of the petroleum-derived VOC under examination. The near coincidence between the excitation wavelength $\lambda e$ and the resonance Raman excitation wavelength can lead to greatly enhanced intensity of the Raman scattering, which may facilitate detection of petroleum-derived VOC, even at low concentrations.

In this way, when a spill 12 of petroleum-derived VOC is present across the UV radiation beam 34, the UV radiation beam 34 interacts with the molecules 18 of the petroleum-derived VOC to generate a return signal 36 having Raman scattering resulting from the resonance Raman interaction. However, when no molecules 18 of petroleum-derived VOC interacts with the UV radiation beam 34, the return signal 36 lacks the Raman scattering and no spill 12 of petroleum-derived VOC is present across the UV radiation beam 34.

In some embodiments, it is envisaged that leaks having a flow rate of 0.1 L/min or less can be detected using the device 10. In some other embodiments, the computer 40 can be used to signal the presence of the spill 12 of petroleum-derived VOC in quasi real time, which can limit the damage to the environment when the pipeline 16 has a leak, for instance.

As will be understood via the examples presented herebelow, the UV radiation generator 30 can be adapted to generate a UV radiation beam 34 having an excitation wavelength $\lambda e$ tuned to any resonance Raman excitation wavelength of any petroleum-derived VOC under examination, depending on the embodiment. A device may be adapted to detect leaks of two or more petroleum-derived VOCs by interrogating the distant target 32 with two or more excitation wavelengths, each of the two or more excitation wavelengths corresponding to a resonance Raman excitation wavelength of respective ones of the two or more petroleum-derived VOCs.

Use of the device 10 to detect spills of petroleum-derived VOC along the pipeline path 28 of a given pipeline can thus be made remotely, without disrupting the normal operation of the given pipeline, and at any desired frequency (e.g., once per day, once per month, once per year).

Figure 2:
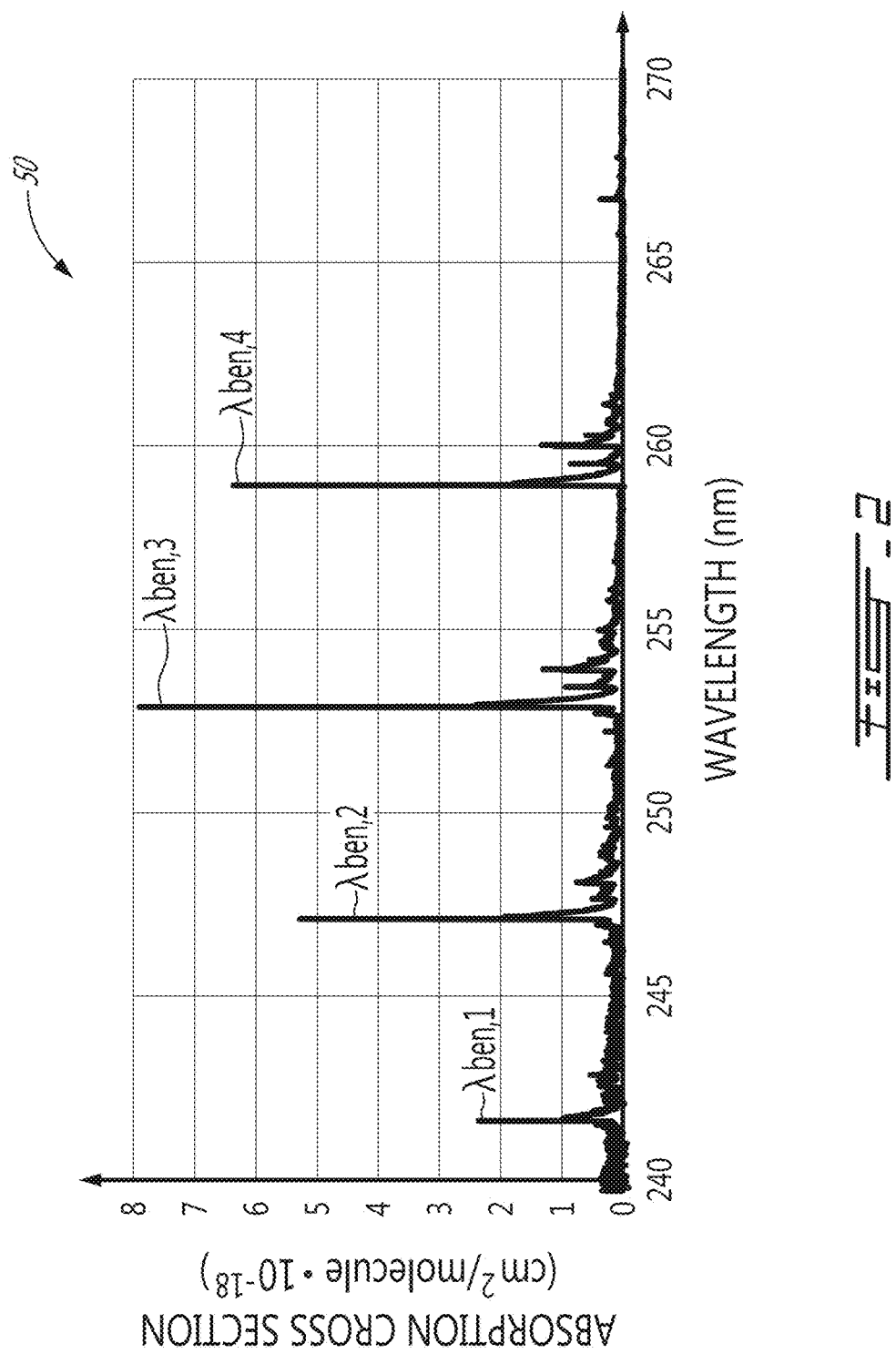
FIG. 2 is a graph showing an example of an absorption spectrum of a benzene molecule, in vapor form, in accordance with an embodiment.

FIG. 2 shows a graph of an example of a first absorption spectrum 50 of a benzene molecule, in accordance with an embodiment.

As depicted, the benzene molecule has a plurality of resonance Raman excitation wavelengths. More specifically, the first absorption spectrum 50 shows that the benzene molecule has a first resonance Raman excitation wavelength $\lambda$ben,1 at about 241.60 nm, a second resonance Raman excitation wavelength $\lambda$ben,2 at about 247.60 nm, a third resonance Raman excitation wavelength $\lambda$ben,3 at about 252.87 nm and a fourth resonance Raman excitation wavelength $\lambda$ben,4 at about 258.92 nm.

In this way, the UV radiation generator 30 can be adapted to generate a UV radiation beam 34 having an excitation wavelength $\lambda$e tuned to at least one of the first, second, third, fourth resonance Raman excitation wavelengths $\lambda$ben,1, $\lambda$ben,2, $\lambda$ben,3 and $\lambda$ben,4 of the benzene molecule in order to cause the desired resonance Raman interaction. As can be understood, the benzene molecule may have other resonance Raman excitation wavelengths which are not shown in FIG. 2.

Figure 3:
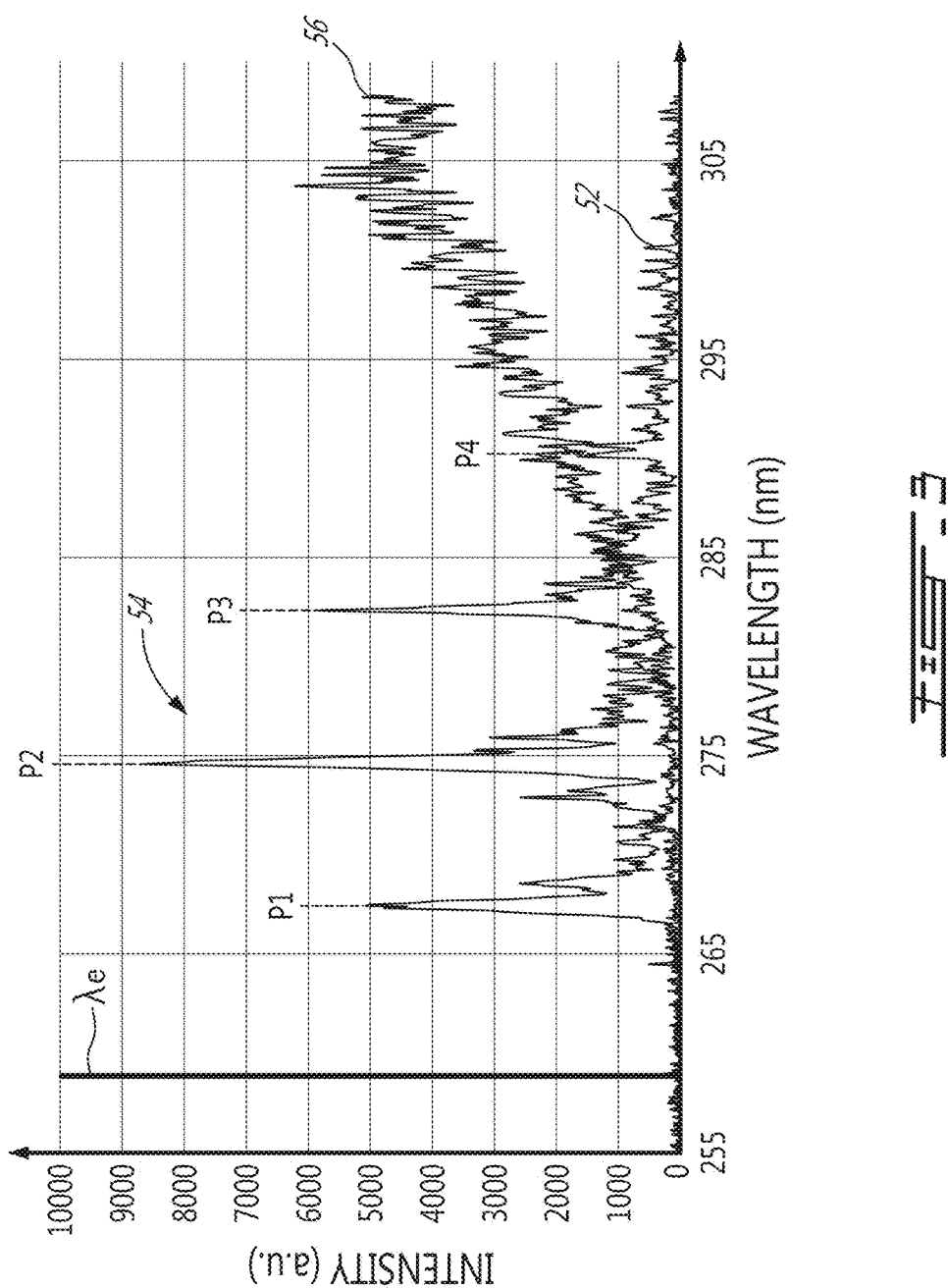
FIG. 3 is a graph showing an example of a return signal including Raman scattering, in accordance with an embodiment.

FIG. 3 shows experimental results of a specific experiment conducted on a sample containing molecules of benzene at a concentration of 10 ppm in air. As shown, an experimental return signal 52 was obtained upon illumination of the sample with a UV radiation beam 34 having an excitation wavelength $\lambda$e tuned to the fourth resonance Raman excitation wavelength $\lambda$ben,4 of the benzene molecule (i.e. $\lambda$e≈259.8 nm). In this example, the UV radiation beam 34 is a UV pulsed laser beam having an emission band $\Delta\lambda$e of about 0.03 nm and a pulse width of 10 ns. The excitation wavelength $\lambda$e was added to the experimental return signal 52 for ease of understanding.

As can be seen in this specific example, the experimental return signal 52 includes a Raman scattering 54 including a first intensity peak P1 at a wavelength of about 268 nm, a second intensity peak P2 at a wavelength of about 275 nm, a third intensity peak P3 at a wavelength of about 283 nm and a fourth intensity peak P4 at a wavelength of about 291 nm. In this example, as can be understood, some of the intensity peaks P1, P2, P3 and P4 can be associated with Raman interaction between the UV radiation beam and nitrogen molecules or oxygen molecules in the air.

In this experiment, it was found convenient to use a radiation beam in the UV region of the electromagnetic spectrum to illuminate the distant target 32 in order to reduce the impact of noise associated with sunlight in the return signal 36, as there is no sunlight shining on the earth's surface below 300 nm. Also, fluorescence generated by the UV radiation beam 34 hitting the earth surface, e.g. grass, is generated at wavelengths usually higher than 260 or 270 nm as shown at 56 in FIG. 3. Fluorescence of rock, sand and earth is not likely to be present below 310 nm.

Indeed, since the Raman scattering 54 is distributed in a given spectral region in the solar blind region of the electromagnetic spectrum, the given spectral portion of the return signal 36 is not likely to be blurred with the noise associated with sunlight.

As can be seen, most of the energy of the Raman scattering 54 is distributed where the noise due to fluorescence of grass such as shown at 56 is relatively low.

Figure 4:
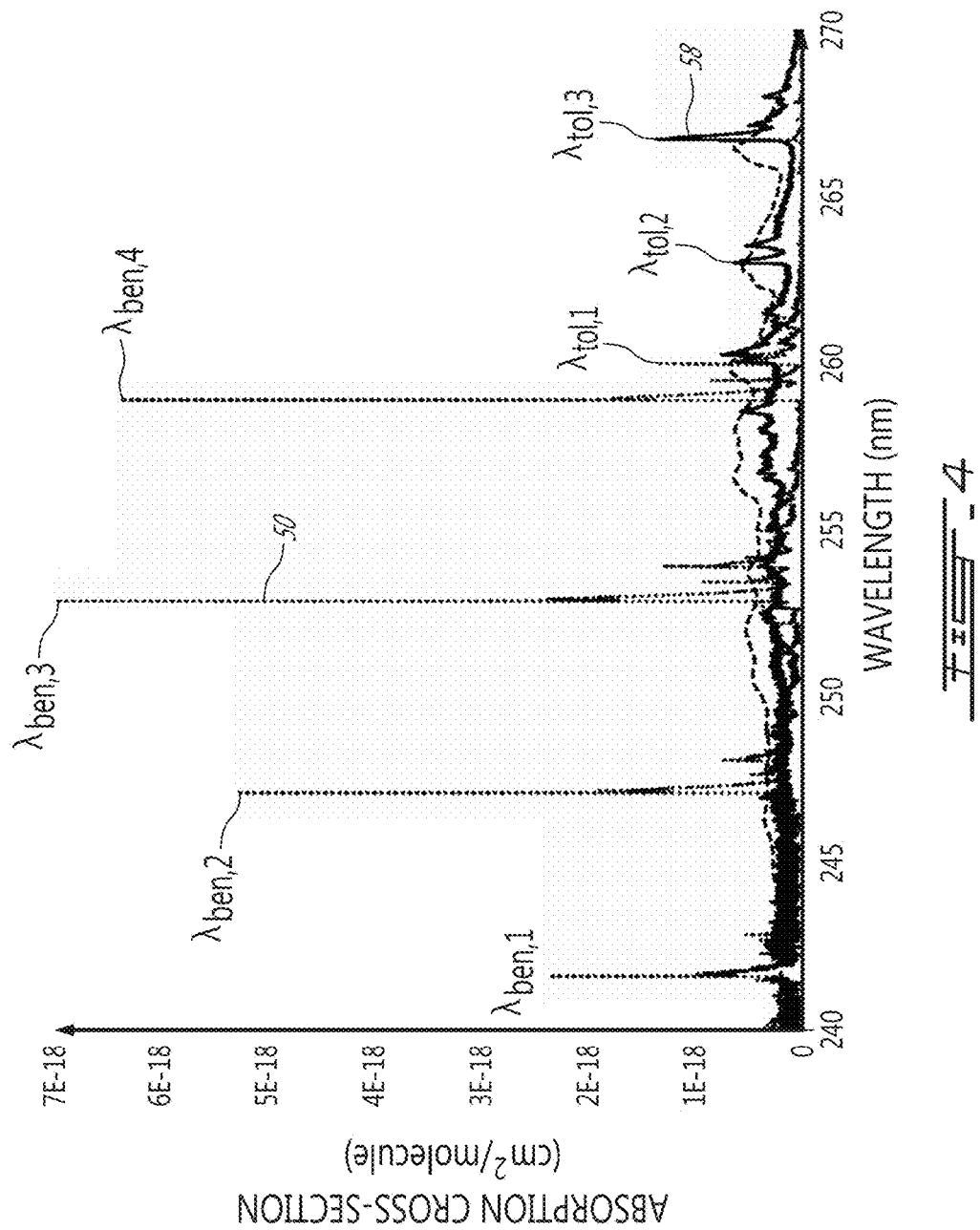
FIG. 4 is a graph showing exemplary absorption spectrums of a benzene molecule, a toluene molecule and an ethylbenzene molecule, in accordance with an embodiment.

FIG. 4 shows a graph of an example of a superposition of the first absorption spectrum 50 for the benzene molecule and a second absorption spectrum 58 for a toluene molecule, in accordance with another embodiment. Data for the benzene molecule and the toluene molecule can be found in the publication "Fally, S., M. Carleer, and A. C. Vandaele, UV Fourier transform absorption cross sections of benzene, toluene, meta-, ortho-, and para-xylene. Journal of Quantitative Spectroscopy and Radiative Transfer, 2009. 110 (9-10): p. 766-782.". Data for the ethylbenzene molecule can be found in the publication "Etzkorn, T., et al., Gas-phase absorption cross sections of 24 monocyclic aromatic hydrocarbons in the UV and IR spectral ranges. Atmospheric Environment, 1999. 33 (4): p. 525-540." The spectrums shown in this graph may have been acquired in different measurement environments and with different measurement systems.

As depicted, the benzene molecule has the first, second, third and fourth resonance Raman excitation wavelengths $\lambda$ben,1, $\lambda$ben,2, $\lambda$ben,3 and $\lambda$ben,4 described above. Additionally, the toluene molecule has a first resonance Raman excitation wavelength $\lambda$tol,1 at about 260.28 nm, a second resonance Raman excitation wavelength $\lambda$tol,2 at about 263.04 nm and a third resonance Raman excitation wavelength $\lambda$tol,3 at about 266.76 nm.

As can be understood, the toluene molecule and the ethylbenzene molecule may have other resonance Raman excitation wavelengths which are not shown in FIG. 4.

In some embodiments, the UV radiation generator 30 can be adapted to generate a UV radiation beam 34 having an excitation wavelength $\lambda$e tuned to at least one of any one of the resonance Raman excitation wavelengths of the benzene molecule. In some other embodiments, the UV radiation generator 30 can be adapted to generate a UV radiation beam 34 having an excitation wavelength $\lambda$e tuned to any one of the resonance Raman excitation wavelengths of the toluene molecule. In alternate embodiments, the UV radiation generator 30 can be adapted to generate a UV radiation beam 34 having an excitation wavelength $\lambda$e tuned to any one of the resonance Raman excitation wavelengths of the ethylbenzene molecule.

Figure 5:
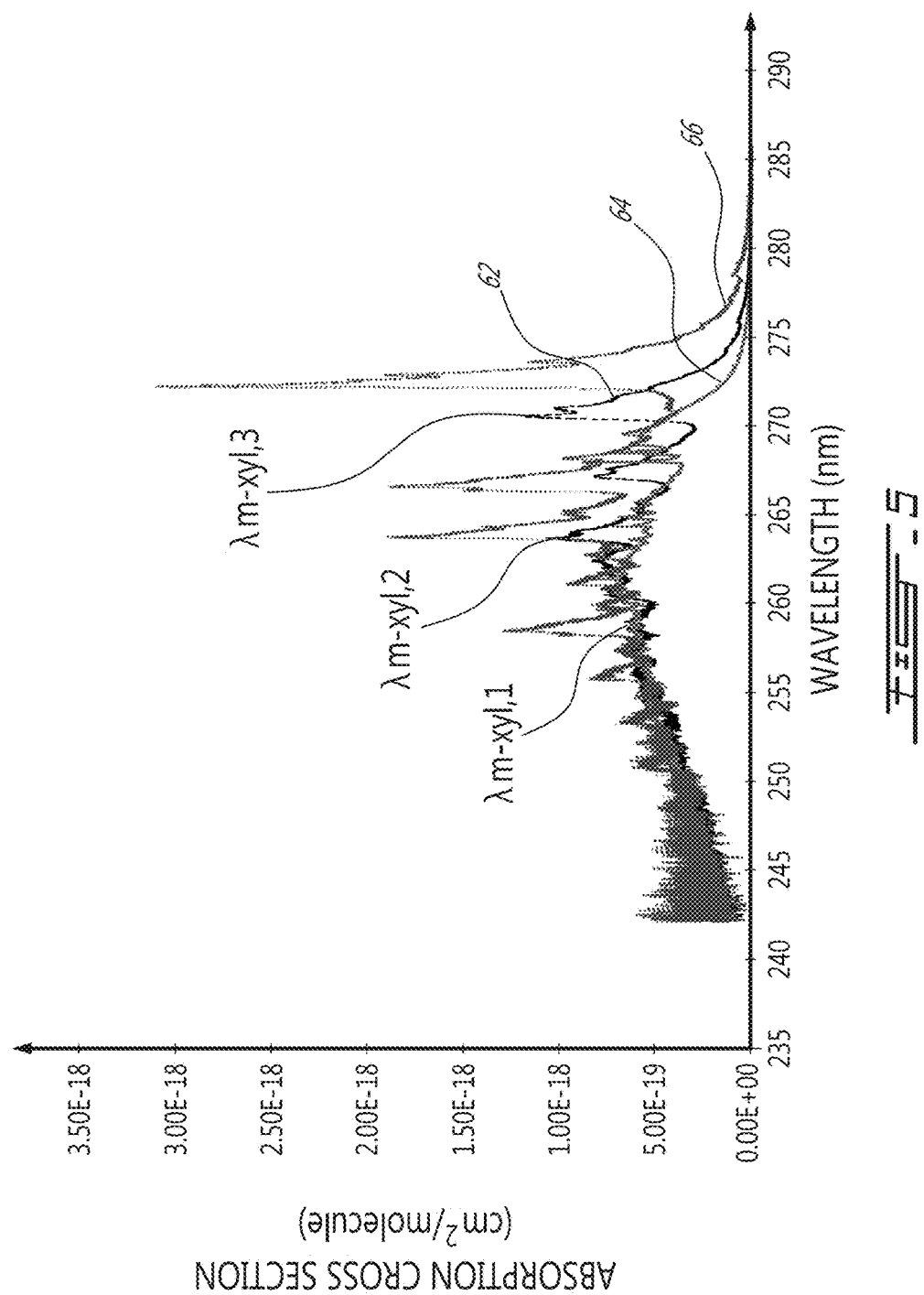
FIG. 5 is a graph shown exemplary absorption spectrums of an m-xylene molecule, an o-xylene molecule and a p-xylene molecule, in accordance with an embodiment.

FIG. 5 shows a graph of an example of a superposition of a fourth absorption spectrum 62 for a m-xylene molecule, a fifth absorption spectrum 64 for an o-xylene molecule and a sixth absorption spectrum 66 for a p-xylene molecule, in accordance with another embodiment.

As depicted, the m-xylene molecule has a first absorption wavelength that can be a resonance Raman excitation wavelength $\lambda$m-xyl,1 at about 258.47 nm, a second absorption wavelength that can be a resonance Raman excitation wavelength $\lambda$m-xyl,2 at about 263.75 nm and a third absorption wavelength that can be a resonance Raman excitation wavelength $\lambda$m-xyl,3 at about 272.22 nm.

In some embodiments, the UV radiation generator 30 can be adapted to generate a UV radiation beam 34 having an excitation wavelength $\lambda$e tuned to at least one of any one of the resonance Raman excitation wavelengths of the m-xylene molecule. In some other embodiments, the UV radiation generator 30 can be adapted to generate a UV radiation beam 34 having an excitation wavelength $\lambda$e tuned to any one of the resonance Raman excitation wavelengths of the o-xylene molecule. In alternate embodiments, the UV radiation generator 30 can be adapted to generate a UV radiation beam 34 having an excitation wavelength $\lambda e$ tuned to any one of the resonance Raman excitation wavelengths of the p-xylene molecule or any other petroleum-derived VOC.

As can be understood, the m-, o- and p-xylene molecules may have other absorption peaks that can be resonance Raman excitation wavelengths which are not shown in FIG. 5.

Figure 6:
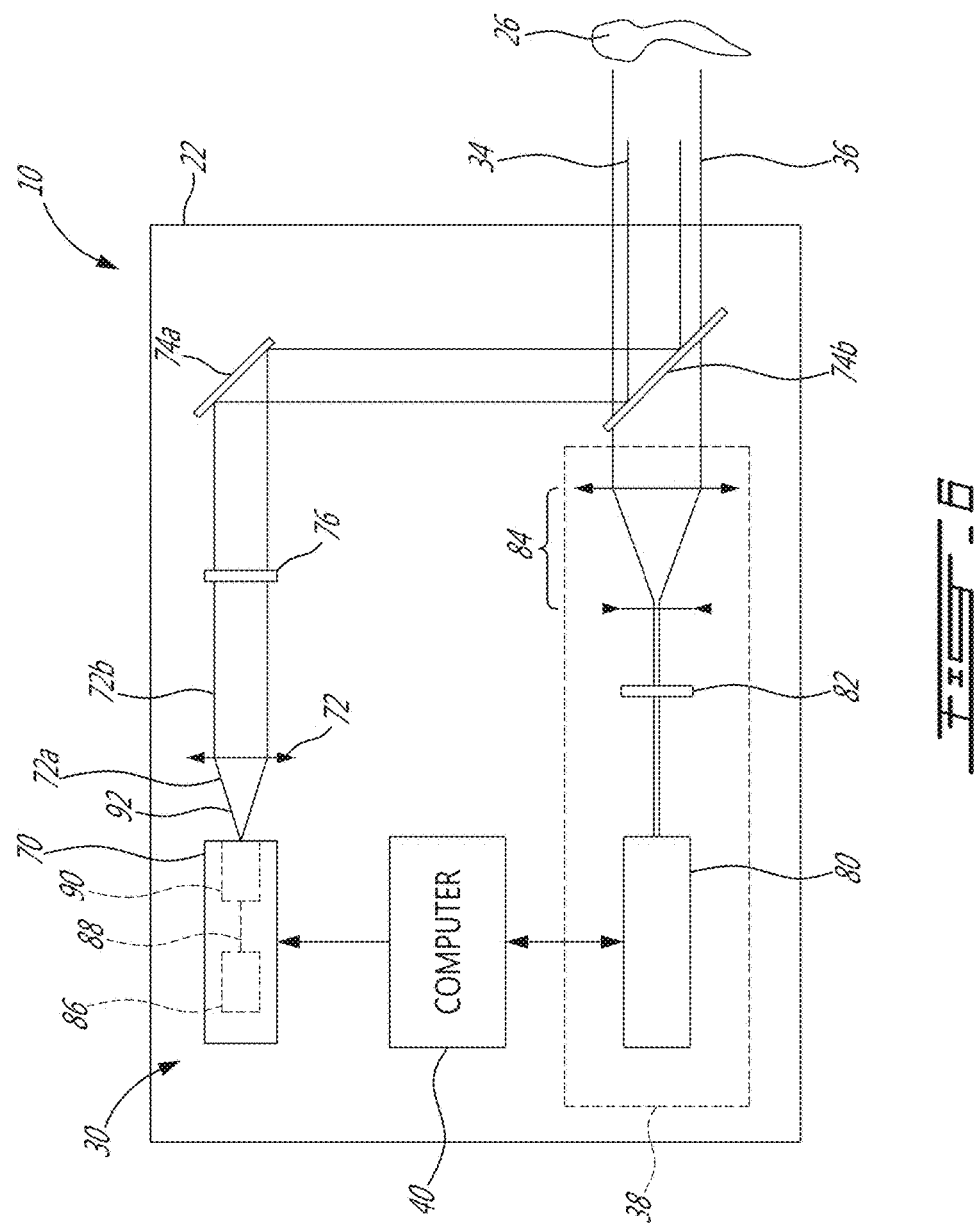
FIG. 6 is a schematic view of the device of FIG. 1, in accordance with an embodiment.

FIG. 6 shows an example of the device 10 for determining the presence of a remote spill of petroleum-derived VOC, in accordance with an embodiment.

As depicted in this illustrated example, the UV radiation generator 30 includes a UV laser source 70 optically coupled with a beam forming element 72 and routing reflective elements 74a and 74b. In this embodiment, the UV laser source 70 is a pulsed UV laser source and, accordingly, the UV radiation beam 34 is a UV pulsed laser beam. The beam forming element 72 can be a diverging element, a collimating element or a focusing element depending on the embodiment.

As shown, the beam forming element 72 is adapted to receive a first laser beam 72a from the UV laser source 70 and to collimate it to provide a second laser beam 72b, generally referred to as the UV radiation beam 34. In the illustrated embodiment, the first laser beam 72a is a diverging beam whereas the second laser beam 72b is a collimated beam. However, in other embodiments, the first and second laser beams 72a and 72b can differ from the illustrated embodiment.

As can be seen, the routing reflective elements 74a and 74b receive the second laser beam 72b and redirect it towards the scene 26 as desired. The number of routing reflective elements may differ from an embodiment to another. For instance, in some embodiments, a UV radiation generator can have no reflective element whereas, in some other embodiments, a UV radiation generator can have either a single one reflective element or more than two routing reflective elements. The routing reflective elements can be provided in the form of scanning heads which are controllable by the computer 40. Scanning heads can be useful in scanning the pipeline path and areas surrounding the pipeline path.

In this example, the UV radiation generator 30 has a first filter element 76 to filter out undesired spectral portions of the spectrum of the UV laser source 70 in order to provide the excitation wavelength $\lambda e$ with a suitably narrow wavelength band $\Delta\lambda e$.

Still referring to FIG. 6, the receiver assembly 38 includes a photomultiplier (PM) tube 80, a second filter element 82 and a telescope 84 optically coupled with one another to receive and monitor the return signal 36. In these embodiments, the photomultiplier tube 80 is adapted to measure an intensity of the filtered return signal. The measured intensity can be indicative of the total (or integrated) amount of energy that reaches the photomultiplier tube 80 and which is within the Raman scattering band of the second filter element 82. As will be understood, a grating spectrometer can be used instead of the filter element 82 or a camera can also be used instead of the PM tube 80 in other embodiments.

As shown in this example, the reflective element 74b is provided in the form of a dichroic element which reflects the excitation wavelength $\lambda e$ towards the scene 26 and that is optically transparent to wavelengths of the Raman scattering higher in wavelength than the excitation wavelength $\lambda e$ such that the return signal 36 can reach the PM tube 80 without letting the excitation wavelength $\lambda e$ reach it.

In this embodiment, the telescope 84 is used to collect as much as possible of the return light 36 and to produce a reduced diameter beam of the return signal 36 to fit the detector or pass through a second filter element 82, and which can be used to filter out undesired spectral portions of the return signal 36. For instance, wavelengths higher than any expected Raman scattering (e.g., >300 nm) may be filtered out using the second filter element 82. Example of filtered wavelengths can include wavelengths associated with the UV radiation beam or noise due to fluorescence of grass for instance.

As shown in this embodiment, the UV laser source 70 includes an Ytterbium-doped fiber laser 86 adapted to generate a fundamental laser beam 88 (e.g., having a fundamental wavelength $\lambda 1$ between 1000 nm and 1100 nm), and a fourth harmonic generator 90 optically coupled with the Ytterbium-doped fiber laser 86 in a manner to generate a fourth harmonic laser beam 92. In these embodiment, the fourth harmonic laser beam 92 corresponds to the UV radiation beam 34 and has a fourth harmonic wavelength $\lambda 4$ corresponding to the fundamental wavelength $\lambda 1$ divided by the number 4.

For instance, when the petroleum-derived VOC is benzene, the fundamental laser beam 88 can have a fundamental wavelength of 1035.6 nm whereas the fourth harmonic laser beam 92 can have a fourth harmonic wavelength of 258.9 nm which corresponds with a resonance Raman excitation wavelength of the benzene molecule, as described above.

UV laser beams having other wavelengths can be generated in any other suitable ways depending on the petroleum-derived VOC under examination and on which resonance Raman excitation wavelength is interrogated.

For instance, still in the case of benzene, using a Nd:YAG laser source or any suitable equivalent may be used to produce a UV laser beam having an excitation wavelength of 258.9 nm.

More specifically, in an embodiment, generating a third harmonic laser beam (e.g., having a third harmonic wavelength of 355 nm or equivalent) from a fundamental laser beam of a Nd:YAG laser source (e.g., having a fundamental wavelength of 1064 nm), pumping an optical parametric oscillator (OPO) with the third harmonic laser beam to generate a green laser beam having a wavelength of about 517.8 nm, and then generating the second harmonic laser beam from the green laser beam to produce a UV laser beam having 258.9 nm may be possible.

However, it will be understood that other suitable UV radiation generator may be used. For instance, short-wave UV lamps, gas discharge lamps, UV light-emitting diodes (LEDs) may be used in some embodiments.

Figure 7:
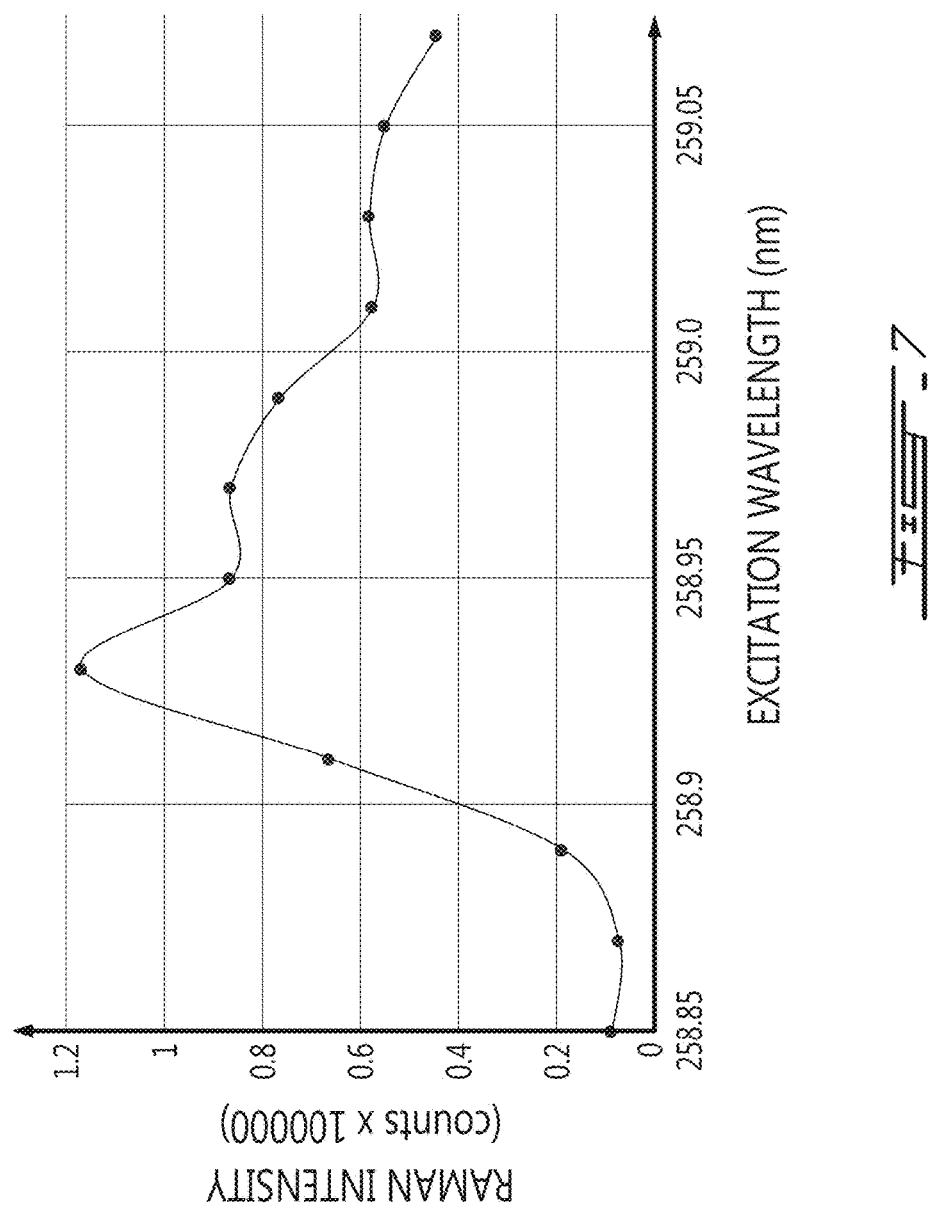
FIG. 7 is a graph showing example Raman emission intensity integrated over a Raman scattering band when molecules of benzene are excited with a radiation beam having one of a plurality of excitation wavelengths.

For instance, FIG. 7 is a graph showing an integrated Raman intensity measured by the photomultiplier tube 80 when a sample containing benzene molecules is excited with a UV radiation beam having an excitation wavelength tunable between 0.25885 µm and 0.25905 µm and a spectral spread at half intensity of approximately 0.00003 µm.

More specifically, it can be seen that when the UV radiation beam having an excitation wavelength of 0.25885 µm excites the sample, the total amount of energy that reaches the photomultiplier tube 80, or the intensity measured by the photomultiplier tube 80, is relatively low (e.g., about 0.1×100000 counts) as compared with when the UV radiation beam has an excitation wavelength of 0.25893 µm. Indeed, when the UV radiation beam has an excitation wavelength tuned to a resonance Raman excitation wavelength of the benzene molecule, the intensity measured by the photomultiplier tube 80 is about 1.2×100000 counts.

In these embodiments, the computer 40 may be configured to determine the presence of a spill of petroleum-derived VOC when the measured intensity is indicative of a resonance Raman interaction between the UV radiation beam and the molecules of the petroleum-derived VOC. The computer 40 can be configured to determine the presence of a spill of petroleum-derived VOC when the measured intensity is above a threshold. For instance, the threshold can be set to about 0.8×100000 counts in the specific embodiment shown in FIG. 7.

Figure 8:
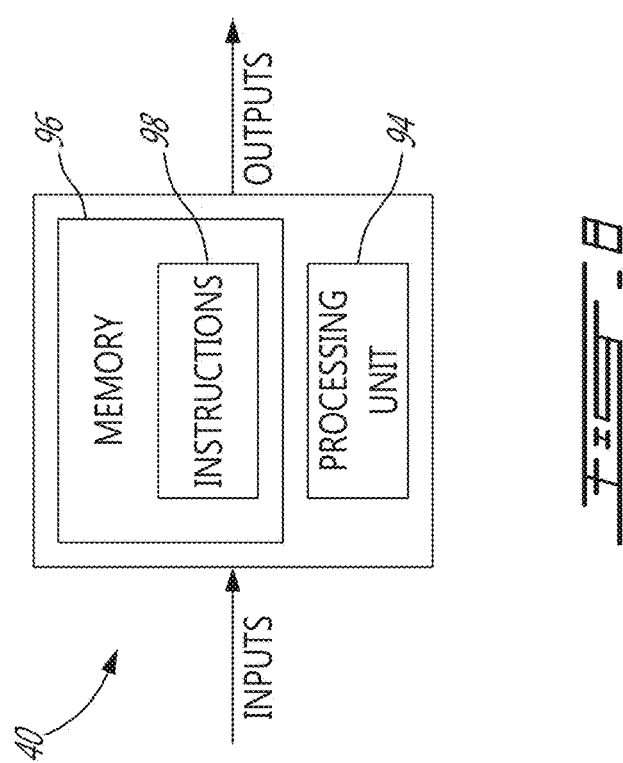
FIG. 8 is a schematic view of an hardware and soft implementation of a computer of the device of FIG. 1, in accordance with an embodiment.

FIG. 8 shows a schematic representation of the computer 40, as a combination of software and hardware components. The computer 40 may be part of the device 10 or be provided externally. In this example, the computer 40 is illustrated with one or more processing units (referred to as "the processing unit 94") and one or more computer-readable memories (referred to as "the memory 96") having stored thereon program instructions 98 configured to cause the processing unit 94 to generate one or more outputs based on one or more inputs. The inputs may comprise one or more signals representative of the instructions to generate the UV radiation beam, the threshold, the excitation wavelength λe, the petroleum-derived VOC under examination, any expected form of Raman scattering, and the like. The outputs may comprise one or more signals representative of the presence or absence of a spill of petroleum-derived VOC at the distant target, a concentration, a mapping indicating the presence or the absence of a spill of petroleum-derived VOC, and/or a concentration thereof, at any suitable spatial location of the scene 26, a warning and the like.

The processing unit 94 may comprise any suitable devices configured to cause a series of steps to be performed so as to implement computer-implemented methods such that the instructions 98, when executed by the computer 40 or other programmable apparatuses, may cause the functions/acts/steps specified in the methods described herein to be executed. The processing unit 94 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 96 may comprise any suitable known or other machine readable storage medium. The memory 96 may comprise non-transitory computer readable storage medium such as, for example, but not limited to, an electronic, magnetic, optical, electromagnetic, infrared, or semiconductor system, apparatus, or device, or any suitable combination of the foregoing. The memory 96 may include a suitable combination of any type of computer memory that is located either internally or externally to device such as, for example, random-access memory (RAM), read-only memory (ROM), compact disc read-only memory (CDROM), electro optical memory, magneto-optical memory, erasable programmable read-only memory (EPROM), and electrically-erasable programmable read-only memory (EEPROM), ferroelectric RAM (FRAM) or the like. The memory 96 may comprise any storage means (e.g., devices) suitable for retrievably storing machine-readable instructions executable by the processing unit 94.

Each computer program described herein may be implemented in a high level procedural or object oriented programming or scripting language, or a combination thereof, to communicate with an engine computer. Alternatively, the programs may be implemented in assembly or machine language. The language may be a compiled or an interpreted language. Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

In some embodiments, the computer 40 identifies Raman scattering in the received return signal 36 in a manner that a presence of the spill 12 of petroleum-derived VOC at the distant target 32 can be determined. In some other embodiments, the computer 40 identifies no Raman scattering in the received return signal 36. In this case, the computer 40 can determine an absence of the spill 12 of petroleum-derived VOC at the distant target 32.

In some embodiments, the computer 40 compares an intensity of the received return signal 36 with a threshold and then identifies Raman scattering in the received return signal 36 when the intensity is above the threshold. In these embodiments, the computer 40 can be configured to signal an alert. In some embodiments, the alert is signalled in real time, in some other embodiments, the alert is stored on a computer-readable memory for latter consultation.

In alternate embodiments, the computer 40 compares the intensity of the Raman scattering with calibration data stored on a computer-readable memory. Indeed, the intensity of the Raman scattering from a vapor plume is generally proportional to the concentration-length product, therefore, calibration data can be obtained. In these embodiments, the computer may generate an output indicative of a concentration-length product of the petroleum-derived VOC in the plume 13. The output can be stored on a computer-readable memory, transmitted to an external computer, or displayed on a user interface.

It is envisaged that the computer 40 can determine a distance, along the UV radiation beam 34, between the receiver assembly 38 (or any reference point relative the aircraft 24 or the ground) and the spill 12 of petroleum-derived VOC or distant target based on a time delay between the generation of the UV radiation beam 34 towards the distant target 32 and the reception of the return signal 36 from the distant target 32.

As it will be understood, in this disclosure, the word "processor" is used broadly so as to encompass one or more processors and other synonyms (such as one or more computers, one or more processing units and the like). Moreover, the expression "computer-implemented" is meant to be implementable by a processor. Accordingly, computer-implemented steps can be executed by a processor.

It will be understood that the expression "computer" as used herein is not to be interpreted in a limiting manner. It is rather used in a broad sense to generally refer to the combination of some form of one or more processing units and some form of memory system accessible by the processing unit(s). A computer can be a personal computer, a smart phone, an appliance computer, etc.

It will be understood that the various functions of the computer, or more specifically of the processing unit or of the memory controller, can be performed by hardware, by software, or by a combination of both. For example, hardware can include logic gates included as part of a silicon chip of the processor. Software can be in the form of data such as computer-readable instructions stored in the memory system. With respect to a computer, a processing unit, a memory controller, or a processor chip, the expression "configured to" relates to the presence of hardware, software, or a combination of hardware and software which is operable to perform the associated functions.

Conventional Raman spectroscopy detection devices when operated in a LIDAR configuration can have a high optical resolution spectrometer as part of their receiver assembly. Such spectrometers may be provided in the form of a grating spectrometer, and often in the form of double or triple monochromators or spectrographs. The spectrometers are used to filter out, as much as possible, Rayleigh scattering associated with the pulsed laser beam by molecules in the air or from scattering by liquid or solid targets in the case of returns from liquid or solid surfaces. In addition, spectrometers may allow for a reduction in interference from other molecules and thus may provide an increase in effective sensitivity when coupled with a very low optical linewidth laser system. In some embodiments, these detection devices have gated imagers in the detection plane of the spectrometers, in the form of intensified charge coupled device cameras (ICCDs). Such conventional Raman spectroscopy detection devices can thus be bulky.

In the case of a molecule having a Raman resonance, the combination of spectrometers and gated imagers may be replaced with a filter element and an intensity detector such as a photomultiplier tube, as described above. Since the resonance Raman excitation wavelengths are associated with gas phase absorption peaks (electronic transitions), methods developed for the absorption approaches to detection can be modified for use in the resonance Raman approach described herein.

Figure 9:
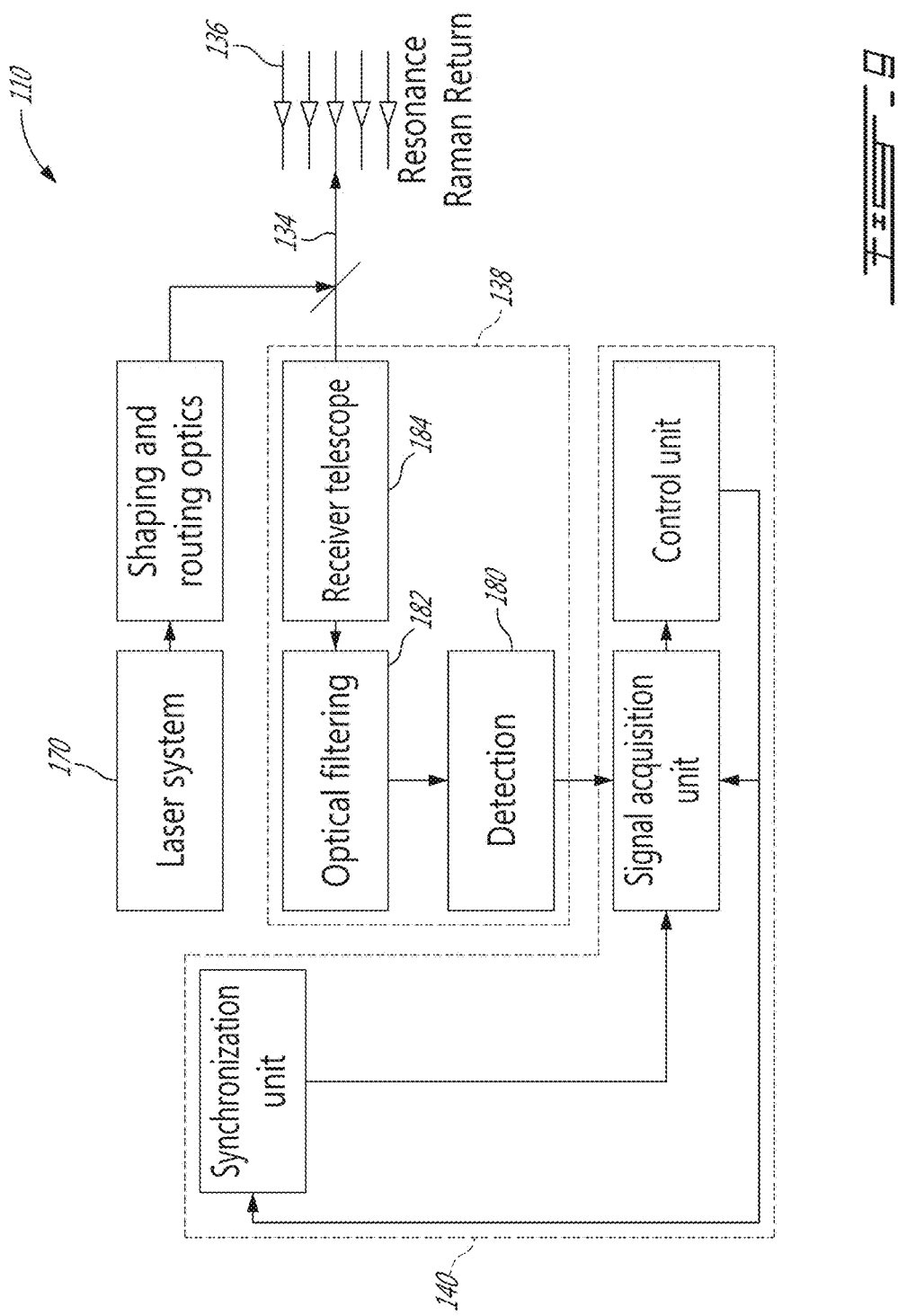
FIG. 9 is a schematic view of another example of a device for determining the presence of petroleum-derived VOC, in accordance with an embodiment.

FIG. 9 shows a schematic view of an example of a device 110 for determining the presence of a petroleum-derived VOC having a Raman resonance in a sample. The sample can be a distant target such as described above, depending on the embodiment. Examples of petroleum-derived VOC having a Raman resonance can include any aromatic compounds (e.g., benzene, toluene). Similar elements bear similar reference numbers, but in the 100 series.

More specifically, the device 110 can be used to illuminate the sample with a radiation beam 134, wherein the radiation beam 134 has an excitation wavelength tuned to a resonance Raman excitation wavelength of the petroleum-derived VOC under examination.

The device 110 can be used to receive a return signal 136 from the sample following said illumination with the radiation beam 134. A filter element 182 is used to filter out, from the return signal 136, wavelengths other than wavelengths of a Raman scattering band of the petroleum-derived VOC for the radiation beam. In other words, when illuminating the sample with the radiation beam 134, Raman light is expected to be found, if the petroleum-derived VOC is present in the sample, in a given Raman scattering band. For instance, if the excitation wavelength of the radiation beam 134 is $\lambda e$, then the Raman scattering band can span between $\lambda e \pm \lambda \lambda 1$ and $\lambda e \pm \lambda 2$, wherein the plus sign is used in case of Stokes waves and the minus sign is used in case of anti-Stokes waves. In the case of Stokes waves, for instance, the filter element 182 is used to filter out wavelengths lower than $\lambda e + \lambda 1$ and wavelengths higher than $\lambda e + \lambda 2$.

The device 110 can be used to measure an intensity of the filtered return signal using an intensity detector such as a photomultiplier tube or a photodiode, for instance, and to determine the presence of the petroleum-derived VOC in the sample when the intensity is indicative of a resonance Raman interaction between the radiation beam and the petroleum-derived VOC.

In this example, the laser source 170 is used in a LIDAR configuration. As can be understood, the pulsed laser beam 134 is shaped so as to have a suitable footprint when it reaches the ground. In this embodiment, the laser beam is routed to beam shaping optics and transmitted along an optical axis. Close to the ground, or on the ground, the pulsed laser beam 134 interacts with the selected petroleum-derived VOC, if any.

With the correct excitation wavelength $\lambda e$, a return signal 136 having an enhanced, more intense Raman scattering can be generated from the interaction of the pulsed laser beam 134 with vapors in the air, liquids or solids on the ground. The return signal 136 travels back to the device 110. A receiver assembly 138, including a telescope 184, collects the return signal 136. The collection telescope 184 and associated optics shape the return signal 136 for further optical processing. A high pass optical interference filter 182 may be provided to reject the scattered laser light and let pass the Raman light of the return signal 136 and any other light at wavelengths above the excitation wavelength $\lambda e$. The return signal 136 can be further optically filtered to let pass light at selected Raman emission wavelengths of the petroleum-derived VOC of interest, rejecting most of the unwanted collected light. This can be done again with band pass interference filters or with a specially designed grating monochromator or polychromator. Finally, the filtered Raman light or any other light in the band pass of the optical filtering elements of the return signal 136 falls onto an optical detector, usually in the form of a photomultiplier tube 180. A camera can also be used in the case of an imaging configuration.

The computer 140 is used to operate the device 110 in a LIDAR configuration, which helps reducing unwanted long lived fluorescence. As shown, the computer 140 has a synchronization unit, a signal acquisition unit and a control unit in this example. Raman light is generated within a few picoseconds. The Raman scattering signal can thus have a temporal shape similar to that of the laser excitation pulse. If the laser excitation pulse is short, say a few hundreds of picoseconds or a few nanoseconds, synchronizing and rapidly gating the detection may allow removal of fluorescence generated at later times. The LIDAR configuration can also allow for spatially resolved standoff detection, enabling the rejection of any return signal generated at distances not of interest and allowing for a better signal to noise ratio for detection of vapors close to the ground (where petroleum-derived VOC can be present since the petroleum-derived VOC may be heavier than air) or for the detection of liquids or solids (e.g., spills) on the ground.

The resonance Raman LIDAR may allow detection, from an altitude of about 100 m, and flying at up to 100 km/h, of amounts of benzene vapor as low as a few hundreds of ppb-m (concentration times distance parameter proportional to total amount of benzene to be detected) above a pipeline path. This may be done in as little as 0.3 second with the device 110 installed in a pod attached to an aircraft. The device 110 may allow low resolution imaging of a selected molecule having a resonance Raman in a terrain such as a pipeline path while scanning the field of view of the device 110 along the terrain.

Figure 10:
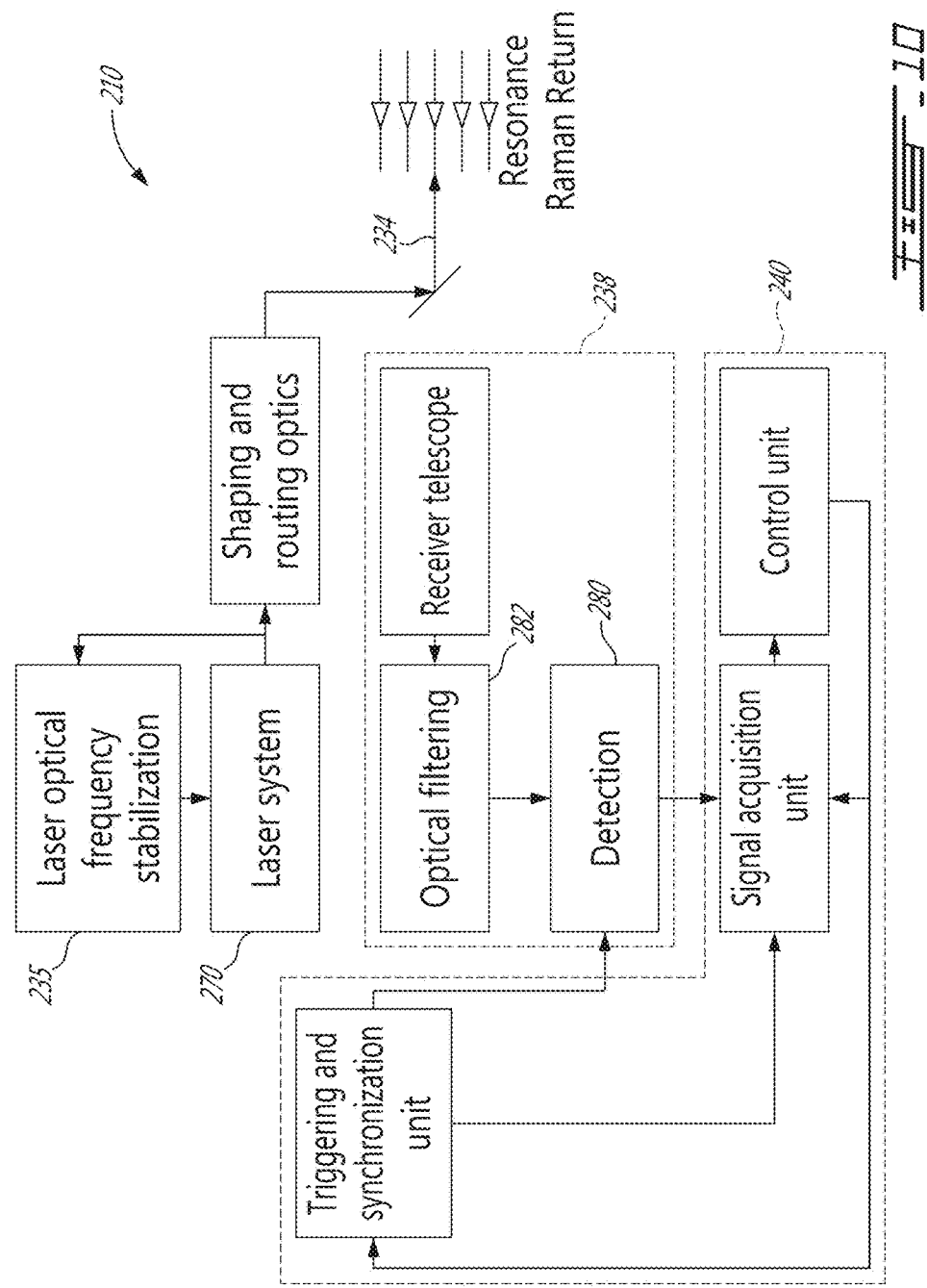
FIG. 10 is a schematic view of another example of a device for determining the presence of a petroleum-derived VOC, shown with a laser optical frequency stabilization subsystem, in accordance with an embodiment.

FIG. 10 shows a schematic view of an example of a device 210 for determining the presence of a petroleum-derived VOC having a resonance Raman in a sample. Similar elements bear similar reference numbers, but in the 200 series.

In this embodiment, the device 210 can be used to illuminate the sample with a first radiation beam, the first radiation beam having a first excitation wavelength being tuned to a resonance Raman excitation wavelength of the petroleum-derived VOC under examination. The device 210 can be used to receive a first return signal from the sample and to measure a first intensity of the first return signal using an intensity detector 280. In this embodiment, the device 210 has a tunable radiation beam generator 270 which can be tuned to any one of the resonance Raman excitation wavelengths of the petroleum-derived VOC under examination.

In this approach, the laser's optical frequency that is on the resonance Raman excitation peak may be stabilized using a laser optical frequency stabilization subsystem 235.

It can be understood that in these embodiments, the filter element 282 is adapted to filter out wavelengths that are not in the Raman scattering band, which is, in this case, selected to cover the Raman light that can be emitted following excitation with the first radiation beam.

As can be understood, the examples described above and illustrated are intended to be exemplary only. The scope is indicated by the appended claims.

What is claimed is:

1. A method of determining the presence of a spill of a petroleum product by the detection of a petroleum-derived volatile organic compound (VOC), the method comprising:
    providing an ultraviolet (UV) radiation generator and a receiver assembly aimed at a scene;
    the UV radiation generator illuminating a distant target in the scene with a UV radiation beam, the UV radiation beam having an excitation wavelength being tuned to a resonance Raman excitation wavelength of the petroleum-derived VOC;
    the receiver assembly receiving a return signal from the distant target; and
    determining the presence of the spill of the petroleum product upon detecting a Raman scattering in the received return signal, the Raman scattering being indicative of a resonance Raman interaction between the UV radiation beam and molecules of the petroleum-derived VOC.

2. The method of claim 1 wherein said receiving includes filtering out, from the return signal, wavelengths other than a Raman scattering band of the petroleum-derived VOC for the UV radiation beam and wherein said detecting includes measuring an intensity of the filtered return signal.

3. The method of claim 1 wherein the petroleum-derived VOC is an aromatic compound.

4. The method of claim 3 wherein the petroleum-derived VOC is benzene having Raman resonances at at least 241.6 nm, 247.6 nm, 252.9 nm and 258.9 nm, the excitation wavelength of the UV radiation beam being tuned to at least one of the Raman resonances of benzene.

5. The method of claim 3 wherein the petroleum-derived VOC is toluene having Raman resonances at at least 260.3 nm, 263 nm and 266.8 nm, the excitation wavelength of the UV radiation beam being tuned to at least one of the Raman resonances of toluene.

6. The method of claim 3 wherein the petroleum-derived VOC is ethylbenzene having Raman resonances at at least 260.2 nm, 263 nm and 266.6 nm, the excitation wavelength of the UV radiation beam being tuned to at least one of the Raman resonances of ethylbenzene.

7. The method of claim 3 wherein the petroleum-derived VOC is m-xylene having Raman resonances at at least 258.5 nm, 263.7 nm and 272.2 nm, the excitation wavelength of the UV radiation beam being tuned to at least one of the Raman resonances of m-xylene.

8. The method of claim 1 wherein said determining includes operating the UV radiation generator and the receiver assembly in a synchronized manner allowing to determine a range-resolved concentration of the petroleum-derived VOC.

9. The method of claim 1 wherein said providing includes flying the UV radiation generator and the receiver assembly over the scene using an aircraft.

10. A device for determining the presence of a spill of petroleum product by the detection of a petroleum-derived volatile organic compound (VOC), the device comprising:
    a housing;
    an ultraviolet (UV) radiation generator mounted to the housing and adapted to illuminate a distant target in a scene with a UV radiation beam, the UV radiation emitter being adapted to generate the UV radiation beam at an emission wavelength tuned to a resonance Raman wavelength of the petroleum-derived VOC;
    a receiver assembly mounted to the housing and adapted to receive a return signal from the distant target; and
    a computer configured to operate the UV radiation emitter and the receiver to determine the presence of the spill of petroleum product upon identifying a Raman scattering in the received return signal, the Raman scattering being indicative of a resonance Raman interaction between the UV radiation beam and molecules of the petroleum-derived VOC.

11. The device of claim 10 wherein the receiver assembly includes an intensity detector adapted to measure an intensity of the received return signal.

12. The device of claim 10 wherein the UV radiation generator and the receiver assembly are operated in a synchronized manner allowing to determine the petroleum-derived VOC at a predetermined range.

13. The device of claim 10 wherein the housing is mountable to a vehicle.

14. The device of claim 13 wherein the vehicle is an aircraft.

15. The device of claim 14 wherein the aircraft is an unmanned aircraft.

16. An aircraft comprising a frame to which is secured the housing of the device of claim 10.

17. A method for determining the presence of a spill of a petroleum product by the detection of a petroleum-derived volatile organic compound (VOC), the method comprising utilizing the device of claim 10.

* * * * *